US011504077B2

(12) United States Patent
Bambot et al.

(10) Patent No.: US 11,504,077 B2
(45) Date of Patent: Nov. 22, 2022

(54) METHODS AND SYSTEMS FOR COMPUTED TOMOGRAPHY TISSUE IMAGING

(71) Applicants: Shabbir Bambot, West Hills, CA (US); Joesph Webster Stayman, Baltimore, MD (US); Andrew Leong, Baltimore, MD (US)

(72) Inventors: Shabbir Bambot, West Hills, CA (US); Joesph Webster Stayman, Baltimore, MD (US); Andrew Leong, Baltimore, MD (US)

( * ) Notice: Subject to any disclaimer, the term of this patent is extended or adjusted under 35 U.S.C. 154(b) by 88 days.

(21) Appl. No.: 17/176,593

(22) Filed: Feb. 16, 2021

(65) Prior Publication Data

US 2021/0251582 A1 Aug. 19, 2021

Related U.S. Application Data

(60) Provisional application No. 62/977,404, filed on Feb. 16, 2020.

(51) Int. Cl.
*A61B 6/00* (2006.01)
*A61B 6/03* (2006.01)
*A61B 6/06* (2006.01)

(52) U.S. Cl.
CPC .............. *A61B 6/06* (2013.01); *A61B 6/032* (2013.01); *A61B 6/4078* (2013.01); *A61B 6/4452* (2013.01); *A61B 6/502* (2013.01); *A61B 6/54* (2013.01)

(58) Field of Classification Search
CPC ... A61B 6/4233; A61B 6/4085; A61B 6/4291; A61B 6/08; A61B 6/06; A61B 6/502; A61B 6/032; A61B 6/54; G02B 27/30; G02B 6/002; G02B 5/005; G02B 27/09
See application file for complete search history.

(56) References Cited

U.S. PATENT DOCUMENTS 4,845,731 A * 7/1989 Vidmar ................. G01T 1/2018
378/146

* cited by examiner

*Primary Examiner* — Don K Wong
(74) *Attorney, Agent, or Firm* — Josef L. Hoffmann; The Small Patent Law Group, LLC (57) ABSTRACT

A method is provided to perform an imaging scan on a target tissue. The imaging scan includes generating a signal directed at a portion of a target tissue using a collimator that includes a slot, wherein a source of a signal assembly is incoherently interrupted. The method also includes receiving at least a portion of the signal from the portion of the target tissue at a linear signal detector positioned directly opposite from the signal assembly with respect to the target tissue, and simultaneously translating the linear signal detector and adjusting a width of the at least one slot of the collimator such that a fan width of the signal at the linear signal detector corresponds to a width of a detector window disposed in the linear signal detector. The method also includes rotating a stage about the target tissue, and repeating performing the imaging scan on the target tissue.

20 Claims, 5 Drawing Sheets

METHODS AND SYSTEMS FOR COMPUTED TOMOGRAPHY TISSUE IMAGING

CROSS-REFERENCE TO RELATED APPLICATIONS

This application claims priority to U.S. Provisional Application Nos. 62/977,404 of which was filed on 16 Feb. 2020, and the entire disclosure of which is incorporated herein by reference.

GOVERNMENT GRANT

This invention was made with government support under contract number 1R43CA224851-01A1 and 1R43CA239777-01 awarded by the National Institutes of Health.

BACKGROUND

Breast cancer is the most commonly diagnosed cancer in women and the second leading cause of cancer death in American women. Screening mammography has been credited for a significant reduction in breast cancer mortality. However, conventional planar mammography has certain limitations. One of these is the representation of three-dimensional (3D) information in a two-dimensional (2D) image. Representation of 3D information in a 2D image introduces a significant error due to tissue superimposition and is a major factor responsible for false positives and missed cancers.

To overcome this limitation, imaging techniques aiming to provide some depth information have been developed. One of these imaging techniques is digital breast tomosynthesis (DBT), which involves acquiring a set of radiographic cone beam projections by moving the x-ray tube over a limited angular range along an arc over the breast and combining these projections to reconstruct a quasi-3D image. DBT has been shown to decrease the recall rate by 15-37% when used for screening and increase the cancer detection rate by 1.2-2.7 per 1000. DBT has sometimes been referred to as "3D" mammography. However, the images are not truly 3D as the third axis is derived from the planar data. Indeed, the performance of DBT is limited by its inability to provide true 3D, isotropic imaging. Further, in-plane DBT resolution is about 10 times higher than the in-depth resolution, leading to a reduced ability to detect and localize lesions.

A different imaging technique, dedicated breast computed tomography (BCT), acquires cone beam projections of the breast over a full 3D 360 degrees to produce a 3D reconstruction of the breast volume. BCT provides improved depth localization of lesions and reduces overlapping features, with the aim of improving diagnostic performance. In general, BCT requires a higher radiation dose due to the increased number of projections. However, dedicated BCT mammography systems have developed low exposure protocols comparable to conventional, planar mammography and/or DBT. Both BCT and DBT images can be used to generate planar mammography images to enable screening in the same device.

However, 3D-capability using radiation exposures comparable to planar mammography has not completely solved the problem of missed or wrongly classified cancer in mammography. This is because the contrast resolution and spatial resolution of BCT (versus mammography and DBT) is limited. Breast cancer presents in mammograms as features such as masses, microcalcifications and architectural distortions. Breast cancer detection is among the most challenging areas in radiography because a high degree of imaging contrast is required to detect the subtle differences in x-ray attenuation due to breast cancer. Injecting an enhancing contrast agent (e.g., iodine) has been suggested, especially in detecting low-grade lesions and for avoiding unnecessary biopsy procedures. Breast cancer detection also requires a high degree of spatial resolution in images (50-100 microns) in order to detect and classify architectural distortions and micro-calcifications. The majority of DCIS (ductal carcinoma in situ) present with microcalcifications and these are also the sole feature used in detecting approximately 40% of all mammary carcinomas. BCT using cone beam radiation is unable to detect cancers smaller than 250-300 microns due to its limited spatial resolution whereas planar mammography and DBT are both capable of visualizing microcalcifications smaller than 100 microns in size. Thus present day BCT spatial resolution limits its clinical potential.

Accordingly, a need exists for methods, devices, and systems to improve image resolution and contrast, while reducing noise and radiation dose, in BCT.

SUMMARY OF THE INVENTION

In one or more embodiments a method is provided that includes, under control of one or more processors configured with executable instructions, performing an imaging scan on a target tissue. The imaging scan on the target tissue includes generating a signal directed at a portion of a target tissue using a collimator of a signal assembly, the collimator including at least one slot, wherein a source of the signal assembly is incoherently interrupted. The method also includes receiving at least a portion of the signal from the portion of the target tissue at a linear signal detector positioned directly opposite from the signal assembly with respect to the target tissue, and simultaneously translating the linear signal detector and adjusting a width of the at least one slot of the collimator such that a fan width of the signal at the linear signal detector corresponds to a width of a detector window disposed in the linear signal detector. The method also includes rotating a stage upon which the signal assembly and the linear signal detector are positioned about the target tissue, and repeating performing the imaging scan on the target tissue.

In one or more embodiments, a system is provided that may include a rotating stage, and a signal assembly positioned on the rotating stage. The signal assembly may include a source configured to be incoherently interrupted and a collimator including at least one slot, wherein the slot is configured to have a width that is adjustable. The signal assembly may also include a linear signal detector positioned on the rotating stage directly opposite from the signal assembly. The linear signal detector may include a detector window disposed therein, wherein the linear signal detector is movable along an axis perpendicular to a signal axis. In addition, the width of the single slot collimator is adjusted simultaneously with translation of the linear signal detector such that a fan width of the signal at the linear signal detector corresponds to a width of the detector window.

In one or more embodiments, a computer program product is provided that may include a non-transitory computer readable storage medium comprising computer executable code. The computer executable code performs an imaging scan on a target tissue. To perform the imaging scan the executable code generates a signal directed at a portion of a target tissue using a collimator of a signal assembly. The collimator may include at least one slot, wherein a source of the signal assembly is incoherently interrupted. To perform the imagine scan the executable code may also receive at least a portion of the signal from the portion of the target tissue at a linear signal detector positioned directly opposite from the signal assembly with respect to the target tissue, and simultaneously translate the linear signal detector and adjust a width of the single slot collimator to such that a fan width of the signal at the linear signal detector corresponds to a width of a detector window disposed in the linear signal detector. The executable code may also rotate a stage upon which the signal assembly and the linear signal detector are positioned about the target tissue, and repeat performing the imaging scan on the target tissue.

DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, and/or the like. In other instances, well-known structures, materials, or operations are not shown or described in detail to avoid obfuscation. The following description is intended only by way of example and simply illustrates certain example embodiments.

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

The present inventors have recognized, among other things, that a problem to be solved can include reducing measurement time in slot-scanning CT (e.g., in whole breast mammography) to improve image resolution and image contrast, while reducing radiation dose (e.g., scattered radiation), in BCT. The present subject matter can help provide a solution to this problem, such as by using novel data acquisition schemes in conjunction with slot-scanning technology (SST) in order to reduce or eliminate scattered radiation to increase image contract and resolution, while also reducing measurement time compared to slot-scanning CT using conventional data acquisition schemes.

Figure 1:
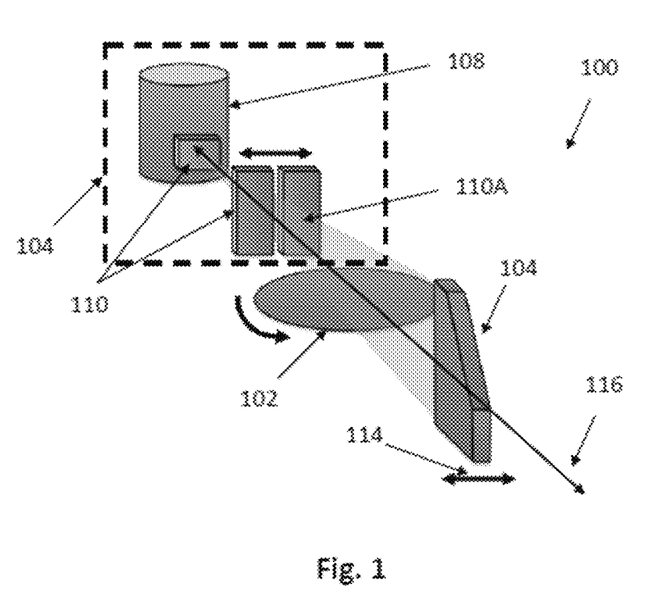
FIG. 1 is a schematic illustrating one example of a slot-scanning CT system in accordance with one or more embodiments herein.
Figure 2:
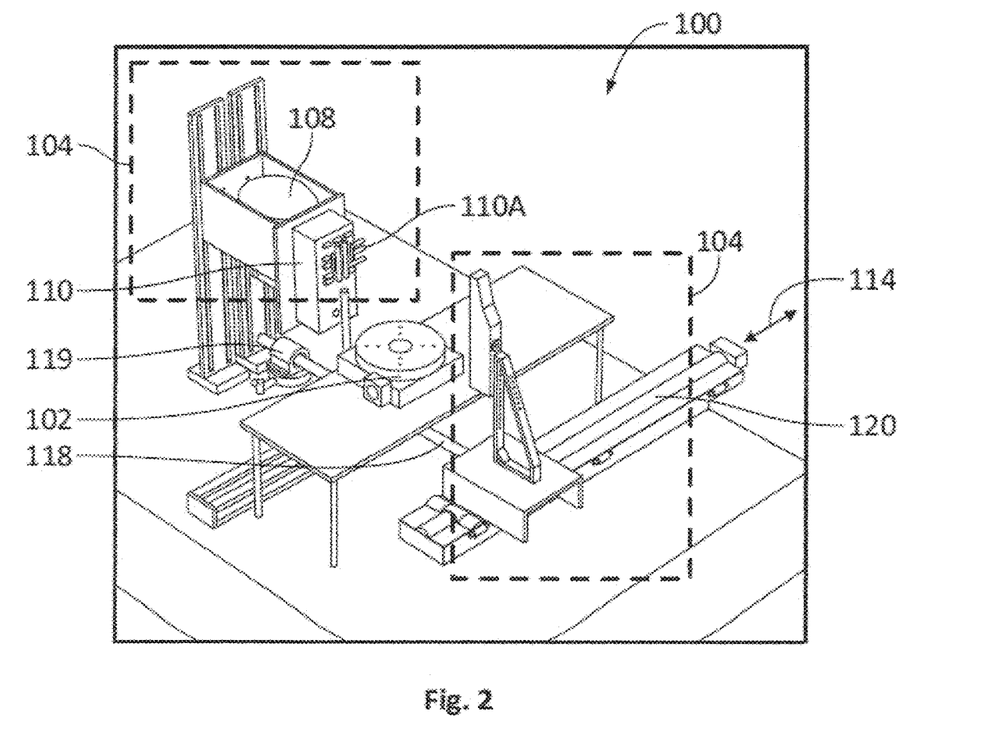
FIG. 2 is a schematic illustrating an example implementation of a slot-scanning CT system in accordance with one or more embodiments herein.

FIG. 1 is a schematic illustrating one example of a slot-scanning CT system in accordance with one or more embodiments herein. FIG. 2 is a schematic illustrating an example implementation of a slot-scanning CT system in accordance with one or more embodiments herein. The slot-scanning CT system 100 includes a rotating stage 102. A signal assembly 104 and a linear signal detector 106 are positioned upon, and rotate with, the rotating stage 102. In FIGS. 1 and 2, an imaging gantry (which the signal assembly 104 and the linear signal detector 106 are coupled to) remains fixed while a target tissue or target tissue phantom being imaged is placed on the rotating stage 102. However, the present inventive subject matter includes an imaging gantry that rotates about a stationary target tissue.

The linear signal detector 106 is positioned on the rotating stage 102 directly opposite from the signal assembly 104. The linear signal detector 106 can include a time delay integration (TDI) detector. The linear signal detector 106 includes a detector window 112 disposed therein. For example, the linear signal detector 106 can be a narrow-slotted image detector. The linear signal detector 106 is movable along an axis 114 perpendicular to a signal axis 116. For example, the linear signal detector 106 is movably positioned on a linear translation stage 120. The linear signal detector 106 can also be movable along an axis perpendicular to a surface of the rotating stage 102.

The signal assembly 104 includes a source 108 and a collimator 110. The source 108 can include an X-ray tube. The source 108 is configured to be pulsed and/or incoherently interrupted. In particular, incoherent interruption is randomly pulsed radiation or radiation that is started, stopped, or interrupted a random times, or spontaneously. The collimator 110 includes a slit assembly 110A that has at least one slot. The collimator 110 can be a single-slot collimator or a multi-slit collimator. The slit assembly 110A of the collimator 110 is configured to have a width (e.g., slot width) that is adjustable. For example, the slit assembly 110A includes a first piece and a second piece that are moveable with respect to each other to adjust the width about and between a minimum width and a maximum width. For example, the signal assembly 104 is configured to generate a thin, tightly collimated X-ray beam to scan the target tissue in precise alignment with the detection window 112 of the linearsignal detector 106. Accordingly, any radiation outside of the X-ray beam volume between the source 108 and the detection window 112 of the linear signal detector 106 is absent from the resultant image data. This virtual elimination of scattered radiation provides significant advantages including high spatial resolution, high contrast and the reduction of required radiation dose (e.g., by up to 67% depending upon breast thickness).

The slot width of the collimator 110 is adjusted simultaneously with translation of the linear signal detector 106 such that a fan width of the signal at the detector window 112 corresponds to a width of the detector window 112. For example, a shaft 118 mechanically couples the first piece and/or the second piece of the slit assembly 110 A of the collimator 110 to the linear signal detector 106 to adjust the width of the slot to ensure the signal fan beam is adjusted in accordance with (e.g., to nominally match) the detector window 112 at all possible positions of the linear signal detector 106. Additionally or alternatively, the linear signal detector106 can move in a direction that is orthogonal to the axis 114, permitting accommodation of changes in target tissue thickness by adjusting the exposure parameters of the imaging scan. Further additionally or alternatively, the first piece and/or the second piece of the collimator 110 can be coupled to and driven by a first motor and the linear signal detector 106 coupled to and driven by a second motor. The first motor and the second motor can be controlled to adjust the width of the slot of the collimator 110 to ensure the signal fan beam is adjusted in accordance with (e.g., to nominally match) the detector window 112 at all possible positions of the linear signal detector 106.

The system also includes memory storing program instructions and one or more processors. The memory stores, as part of the program instructions, a sparse data collection (SDC) application. The one or more processors, in response to execution of the program instructions, implement the SDC application. The SDC application moves the rotating stage 102 about a select number of rotational positions 119 about a target tissue (e.g., breast tissue) positioned between the signal assembly 104 and the linear signal detector 106. The SDC application can move the rotating stage 102 about the select number of rotational positions 119 of the stage relative to the target tissue. The rotating stage 102 can be controlled to move in a stepwise fashion or continuously. The SDC application performs an imaging scan at each of the select rotational positions 119. Performing an imaging scan includes generating a signal (e.g., an X-ray signal) directed at a portion of the target tissue and receiving at least a portion of the signal from the portion of the target tissue at the linear signal detector; simultaneously translating the linear signal detector along an axis perpendicular to a signal axis and adjusting the width of the single slot collimator. The performing can also include generating image data based on the portion of the signal received at the linear signal detector. Optionally, simultaneously translating the linear signal detector includes translating the linear signal detector along an axis perpendicular to the rotating stage.

The SDC application can subsample the image data using, for example, compressed sensing techniques. In one example, the compressed sensing techniques using a slot scanning system are provided by U.S. Pat. No. 9,636,072 to Shores et al. entitled Computed Tomography Breast Imaging And Biopsy System, filed Aug. 28, 2013 that is incorporated in full herein. Subsampling the image data (or collecting sparse data) includes one or more of angular subsampling and radial subsampling. The SDC application can use TDI to construct an image of the target tissue from the incrementally obtained image data. The SDC application can pulse the source 108 and coordinate movement of the collimator 110 (e.g., the width of the slit assembly 110A), the linear detector 106, and the rotating stage 102 to obtain subsets of image data. The SDC application can obtain image data subset both in angles and in radial bins, permitting more incoherent acquisitions consistent with compressed sensing theory. For example, based on using 10% of all projection image data, the SDC application can generate an imaging scan using compressed sensing reconstruction that recovers all the details in the 100% projection image data scenario, greatly reducing both acquired image data and radiation dose. Additionally or alternatively, the SDC application can employ one or more of dictionary and/or patch-based regularization schemes, data-driven priors based on machine learning, or like methods in order to reconstruct sparse image data.

The SDC application repeats the generating, receiving, and simultaneously translating and adjusting across a width of the target tissue at a given rotational position. The SDC application repeats the rotating and performing an imaging scan sequentially until the select number of rotational positions are met. The rotating and performing can be performed in a stepwise fashion. Additionally or alternatively, the rotating and performing are simultaneously and/or continuously executed.

The SDC application and other circuits, systems and methods herein, may be implemented in accordance with the embodiments described in PCT Application Serial No. PCT/US2018/029567, titled "Apparatus and method for digital scan mammography", the complete subject matter of which is incorporated herein by reference in its entirety.

Figure 3:
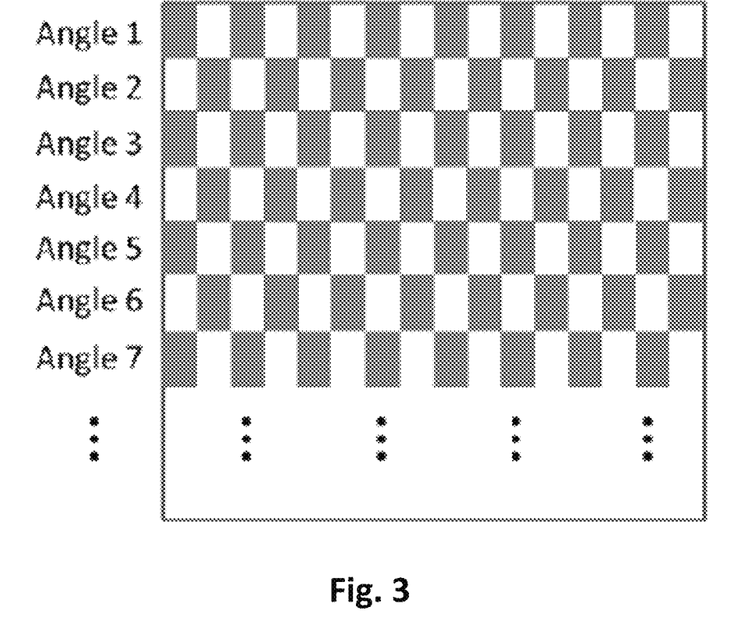
FIG. 3 illustrates one example of a slot-scanning CT scan obtained using pulsed data acquisition in accordance with one or more embodiments herein.

FIG. 3 illustrates one example of a slot-scanning CT scan using pulsed data acquisition in accordance with one or more embodiments herein. FIG. 3 illustrates an imaging scan scheme for, e.g., 50% sparsity using the systems and methods described herein. Here, the SDC application pulses the signal source 108 (e.g., the X-ray tube) at a select duty cycle (e.g., 50%)while performing a two-dimensional (2D) image scan at each of the select number of rotational positions of the rotating stage, followed by a step rotation.

Figure 4:
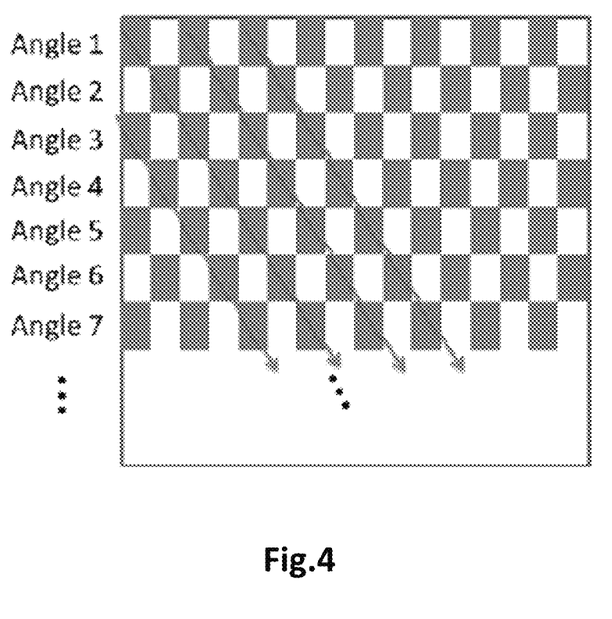
FIG. 4 illustrates one example of a slot-scanning CT scan obtained using continuous data acquisition in accordance with one or more embodiments herein.

FIG. 4 illustrates one example of a slot-scanning CT scan obtained using continuous data acquisition in accordance with one or more embodiments herein. Here, the SDC application performs the image scanning and rotation simultaneously and continuously (without steps) using the systems and methods described herein. The same data can be collected (e.g., over several rotations). For example, the signal source 108 (e.g., the X-ray tube) remains continuously on over a complete 360 degree angular scan, but at each rotational position of the rotating stage only a portion of the radial scan data is captured based on the position of the linear scanner based on the particular angle selected. (Each rotation is depicted by a red arrow in FIG. 4.)

The SDC application can tailor the amount (e.g., %) of sparsity, via user-selected and/or programmed settings, using the parameters of angular vs. radial motor actuation and the duty cycle of the x-ray tube.

Figure 5:
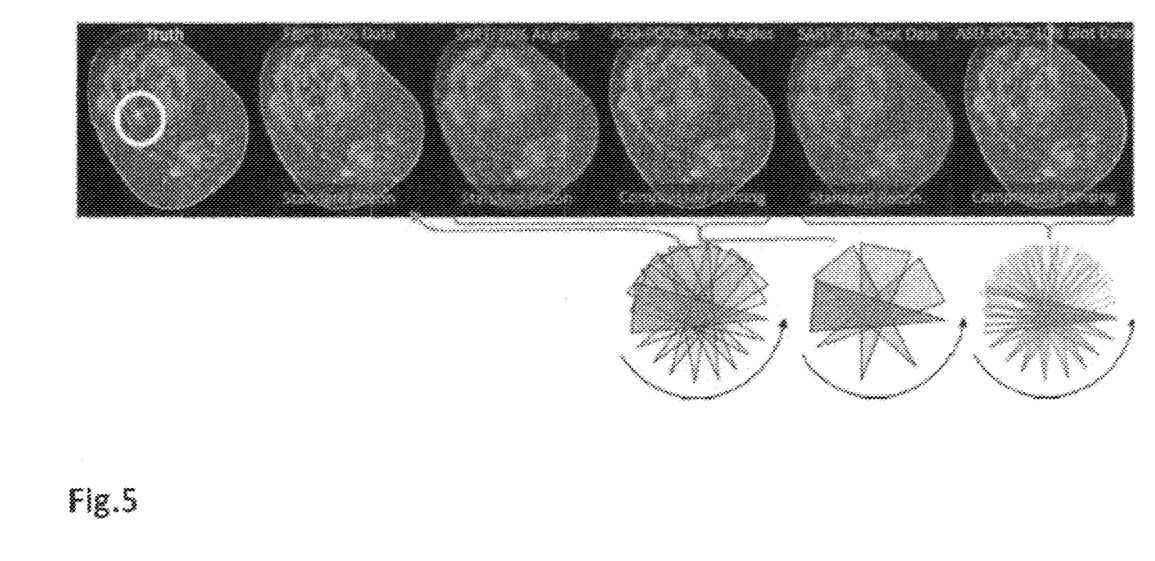
FIG. 5 illustrates slot-scanning CT scans performed in accordance with one or more embodiments herein compared to conventional techniques.

FIG. 5 illustrates a series of slot-scanning CT scans performed using BCT and standard techniques and compressed sensing techniques, both using angular or radial subsampling. A digital breast phantom with a calcification (circled) and an FBP reconstruction using full 360° data is shown. Most studies of under sampled cone beam BCT select an angular subset of complete projection images. Reconstructions using both standard (SART) and compressed sensing (ASD-POCS) approaches show noticeable image quality degradations when only 10% of angles are used. Though compressed sensing performs better, reduced conspicuity of the calcification is evident. In contrast the systems and methods described herein perform slot-scanning CT subset both in angles and in radial bins within projections, permitting more incoherent acquisitions consistent with compressed sensing that recover all of the details in the 100% image data scenario, thereby affording image data and radiation dose reduction in slot-scanning CT. Accordingly, the systems and methods described herein enable obtaining low scatter, high-resolution image data with the advantages of 3D imaging while reducing both image data acquisition time and radiation dose.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

The following numbered Examples are example embodiments of the present inventive subject matter in accordance with embodiments herein:

Example 1 is a method, comprising: under control of one or more processors configured with executable instructions: performing an imaging scan on a target tissue, comprising: generating a signal directed at a portion of a target tissue using a collimator of a signal assembly, the collimator including at least one slot, wherein a source of the signal assembly is incoherently interrupted; and receiving at least a portion of the signal from the portion of the target tissue at a linear signal detector positioned directly opposite from the signal assembly with respect to the target tissue; simultaneously translating the linear signal detector and adjusting a width of the at least one slot of the collimator such that a fan width of the signal at the linear signal detector corresponds to a width of a detector window disposed in the linear signal detector; and rotating a stage upon which the signal assembly and the linear signal detector are positioned about the target tissue; repeating performing the imaging scan on the target tissue.

In Example 2, the subject matter of Example 1 includes, wherein performing includes generating image data based on the portion of the signal received at the linear signal detector.

In Example 3, the subject matter of Example 2 includes, subsampling the image data.

In Example 4, the subject matter of Example 3 includes, wherein the subsampling includes one or more of angular subsampling and radial subsampling.

In Example 5, the subject matter of Examples 1-4 includes, wherein the generating, receiving, and simultaneously translating and adjusting are repeated across a width of the target tissue.

In Example 6, the subject matter of Examples 1-5 includes, wherein the repeating performing the imaging scan continues until a select number of rotational positions of the stage relative to the target tissue are met.

In Example 7, the subject matter of Examples 1-6 includes, wherein the signal is an X-ray signal.

In Example 8, the subject matter of Examples 1-7 includes, wherein the target tissue is breast tissue.

Example 9 is a system, comprising: a rotating stage; a signal assembly positioned on the rotating stage, the signal assembly including source configured to be incoherently interrupted and a collimator including at least one slot, wherein the slot is configured to have a width that is adjustable; and a linear signal detector positioned on the rotating stage directly opposite from the signal assembly, the linear signal detector including a detector window disposed therein, wherein the linear signal detector is movable along an axis perpendicular to a signal axis; wherein the width of the single slot collimator is adjusted simultaneously with translation of the linear signal detector such that a fan width of the signal at the linear signal detector corresponds to a width of the detector window.

In Example 10, the subject matter of Example 9 includes, memory storing program instructions; and one or more processors, in response to execution of the program instructions, to perform the following: rotate the rotating stage about a select number of rotational positions; and perform an imaging scan on a target tissue positioned between the signal assembly and the linear signal detector at each one of the select rotational positions, the perform including: generate a signal directed at a portion of the target tissue; receive at least a portion of the signal from the portion of the target tissue at the linear signal detector; and simultaneously translate the linear signal detector and adjust the width of the single slot collimator.

In Example 11, the subject matter of Example 10 includes, wherein the one or more processors repeat the generate, receive, and simultaneously translate and adjust across a width of the target tissue.

In Example 12, the subject matter of Examples 10-11 includes, wherein the one or more processors repeat the rotate and perform sequentially until a select number of rotational positions of the stage relative to the target tissue are met.

In Example 13, the subject matter of Examples 10-12 includes, wherein the one or more processors continuously and simultaneously execute the move and perform.

In Example 14, the subject matter of Examples 10-13 includes, wherein the target tissue is breast tissue.

In Example 15, the subject matter of Examples 10-14 includes, wherein the linear signal detector is translatable along an axis perpendicular to the rotating stage, and wherein simultaneously translating also includes translating the linear signal detector along the axis perpendicular to the rotating stage.

In Example 16, the subject matter of Examples 9-15 includes, wherein the signal is an X-ray signal.

Example 17 is a computer program product comprising a non-transitory computer readable storage medium comprising computer executable code to: perform an imaging scan on a target tissue, comprising: generate a signal directed at a portion of a target tissue using a collimator of a signal assembly, the collimator including at least one slot, wherein a source of the signal assembly is incoherently interrupted; receive at least a portion of the signal from the portion of the target tissue at a linear signal detector positioned directly opposite from the signal assembly with respect to the target tissue; and simultaneously translate the linear signal detector and adjust a width of the single slot collimator to such that a fan width of the signal at the linear signal detector corresponds to a width of a detector window disposed in the linear signal detector; and rotate a stage upon which the signal assembly and the linear signal detector are positioned about the target tissue; and repeat performing the imaging scan on the target tissue.

In Example 18, the subject matter of Example 17 includes, wherein, as part of the perform, the executable code to generate image data based on the portion of the signal received at the linear signal detector.

In Example 19, the subject matter of Examples 17-18 includes, the executable code to repeat the generate, receive, and simultaneously translate and adjust across a width of the target tissue.

In Example 20, the subject matter of Examples 17-19 includes, the executable code to continue the repeat performing the imaging scan until a select number of rotational positions of the stage relative to the target tissue are met.

In Example 21, the subject matter of Examples 17-20 includes, the computer executable code to subsample the image data.

In Example 22, the subject matter of Example 21 includes, the computer executable code to one or more of angular subsample and radial subsample the image data.

Example 23 is at least one machine-readable medium including instructions that, when executed by processing circuitry, cause the processing circuitry to perform operations to implement of any of Examples 1-22.

Example 24 is an apparatus comprising means to implement of any of Examples 1-22.

Example 25 is a system to implement of any of Examples 1-22.

Example 26 is a method to implement of any of Examples 1-22.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. A method, comprising:
    under control of one or more processors configured with executable instructions: performing an imaging scan on a target tissue, comprising:
    generating a signal directed at a portion of a target tissue using a collimator of a signal assembly, the collimator including at least one slot, wherein a source of the signal assembly is incoherently interrupted; and
    receiving at least a portion of the signal from the portion of the target tissue at a linear signal detector positioned directly opposite from the signal assembly with respect to the target tissue;
    simultaneously translating the linear signal detector and adjusting a width of the at least one slot of the collimator such that a fan width of the signal at the linear signal detector corresponds to a width of a detector window disposed in the linear signal detector; and
    rotating a stage upon which the signal assembly and the linear signal detector are positioned about the target tissue;
    repeating performing the imaging scan on the target tissue.

2. The method of claim 1, wherein performing includes generating image data based on the portion of the signal received at the linear signal detector.

3. The method of claim 2, further comprising subsampling the image data; wherein the subsampling includes one or more of angular subsampling and radial subsampling.

4. The method of claim 1, wherein the generating, receiving, and simultaneously translating and adjusting are repeated across a width of the target tissue.

5. The method of claim 1, wherein the repeating performing the imaging scan continues until a select number of rotational positions of the stage relative to the target tissue are met.

6. The method of claim 1, wherein the signal is an X-ray signal.

7. The method of claim 1, wherein the target tissue is breast tissue.

8. A system, comprising:
    a rotating stage;
    a signal assembly positioned on the rotating stage, the signal assembly including source configured to be incoherently interrupted and a collimator including at least one slot, wherein the slot is configured to have a width that is adjustable; and
    a linear signal detector positioned on the rotating stage directly opposite from the signal assembly, the linear signal detector including a detector window disposed therein, wherein the linear signal detector is movable along an axis perpendicular to a signal axis;
    wherein the width of the single slot collimator is adjusted simultaneously with translation of the linear signal detector such that a fan width of the signal at the linear signal detector corresponds to a width of the detector window.

9. The system of claim 8, further comprising: memory storing program instructions; and one or more processors, in response to execution of the program instructions, to perform the following:
    rotate the rotating stage about a select number of rotational positions; and
    perform an imaging scan on a target tissue positioned between the signal assembly and the linear signal detector at each one of the select rotational positions, the perform including:
    generate a signal directed at a portion of the target tissue;
    receive at least a portion of the signal from the portion of the target tissue at the linear signal detector; and
    simultaneously translate the linear signal detector and adjust the width of the single slot collimator.

10. The system of claim 9, wherein the one or more processors repeat the generate, receive, and simultaneously translate and adjust across a width of the target tissue.

11. The system of claim 9, wherein the one or more processors repeat the rotate and perform sequentially until a select number of rotational positions of the stage relative to the target tissue are met.

12. The system of claim 9, wherein the one or more processors continuously and simultaneously execute the move and perform.

13. The system of claim 9, wherein the target tissue is breast tissue.

14. The system of claim 9, wherein the linear signal detector is translatable along an axis perpendicular to the rotating stage, and wherein simultaneously translating also includes translating the linear signal detector along the axis perpendicular to the rotating stage.

15. The system of claim 8, wherein the signal is an X-ray signal.

16. A computer program product comprising a non-transitory computer readable storage medium comprising computer executable code to:

perform an imaging scan on a target tissue, comprising:

generate a signal directed at a portion of a target tissue using a collimator of a signal assembly, the collimator including at least one slot, wherein a source of the signal assembly is incoherently interrupted;

receive at least a portion of the signal from the portion of the target tissue at a linear signal detector positioned directly opposite from the signal assembly with respect to the target tissue;

simultaneously translate the linear signal detector and adjust a width of the single slot collimator to such that a fan width of the signal at the linear signal detector corresponds to a width of a detector window disposed in the linear signal detector; and rotate a stage upon which the signal assembly and the linear signal detector are positioned about the target tissue; and repeat performing the imaging scan on the target tissue.

17. The computer program product of claim 16, wherein, as part of the perform, the executable code to generate image data based on the portion of the signal received at the linear signal detector.

18. The computer program product of claim 16, the executable code to repeat the generate, receive, and simultaneously translate and adjust across a width of the target tissue.

19. The computer program product of claim 16, the executable code to continue the repeat performing the imaging scan until a select number of rotational positions of the stage relative to the target tissue are met.

20. The computer program product of claim 16, the computer executable code to subsample the image data, and to one or more of angular subsample and radial subsample the image data.

* * * * *